US012773510B2

(12) United States Patent
Schnell

(10) Patent No.: US 12,773,510 B2
(45) Date of Patent: Oct. 27, 2026

(54) DEVICE FOR PERCUTANEOUS DILATIONAL TRACHEOTOMY

(71) Applicant: Coloplast A/S, Humlbaek (DE)

(72) Inventor: Ralf Schnell, Seligenstadt (DE)

(73) Assignee: Coloplast A/S, Humlebaek (DK)

( * ) Notice: Subject to any disclaimer, the term of this patent is extended or adjusted under 35 U.S.C. 154(b) by 935 days.

(21) Appl. No.: 17/802,332

(22) PCT Filed: Feb. 17, 2021

(86) PCT No.: PCT/EP2021/053808
§ 371 (c)(1),
(2) Date: Aug. 25, 2022

(87) PCT Pub. No.: WO2021/170457
PCT Pub. Date: Sep. 2, 2021

(65) Prior Publication Data

US 2023/0102704 A1 Mar. 30, 2023

(30) Foreign Application Priority Data

Feb. 26, 2020 (DE) ..................... 10 2020 105 048.8

(51) Int. Cl.
*A61M 16/04* (2006.01)
*A61M 25/09* (2006.01)

(52) U.S. Cl.
CPC ......... *A61M 16/0472* (2013.01); *A61M 25/09* (2013.01)

(58) Field of Classification Search
CPC .. A61M 16/00; A61M 16/0003; A61M 16/04; A61M 16/0465; A61M 16/0472;
(Continued)

(56) References Cited

U.S. PATENT DOCUMENTS 3,788,326 A * 1/1974 Jacobs .................. A61M 16/00 604/161
4,677,978 A * 7/1987 Melker ............. A61M 16/0472 128/207.29

(Continued)

FOREIGN PATENT DOCUMENTS

DE 102005006276 A1 8/2006
EP 2301618 A1 3/2011

OTHER PUBLICATIONS

TRACOE medical GmbH: Product Catalog Quality by People for People, 30 pages.

*Primary Examiner* — Colin W Stuart
(74) *Attorney, Agent, or Firm* — Coloplast Corp., Coloplast A/S; Nick Baumann

(57) ABSTRACT

To be able to prevent a situation in which, in percutaneous dilational tracheostomy, the guide catheter already inserted into the trachea can kink, a device for percutaneous dilational tracheostomy is disclosed which has a puncture needle, a guide catheter and a guidewire. The puncture needle has a ground tip at its distal end. The maximum external diameter of the puncture needle is smaller than the minimum internal diameter of the guide catheter, and the puncture needle is insertable so far into the guide catheter that the ground tip of the puncture needle protrudes beyond the distal end of the guide catheter. The maximum diameter of the guidewire is smaller than the minimum internal diameter of the puncture needle, with the result that the guidewire can be guided through the puncture needle such that its end protrudes beyond the ground tip of the puncture needle.

13 Claims, 5 Drawing Sheets

(58) Field of Classification Search
CPC ... A61M 39/00–288; A61M 25/00–2025/1097
See application file for complete search history.

(56) References Cited

U.S. PATENT DOCUMENTS

| | | | | | |
|---|---|---|---|---|---|
| 4,834,718 | A | | 5/1989 | McDonald | |
| 5,055,107 | A | * | 10/1991 | Lester | A61M 16/0472 128/207.29 |
| 5,169,387 | A | | 12/1992 | Kronner | |
| 5,507,279 | A | * | 4/1996 | Fortune | A61M 16/0472 128/207.29 |
| 6,109,264 | A | * | 8/2000 | Sauer | A61M 29/02 128/207.29 |
| 2002/0066453 | A1 | * | 6/2002 | Ciaglia | A61M 16/0472 128/207.29 |
| 2003/0114871 | A1 | * | 6/2003 | Turnbull | A61M 16/0472 606/190 |
| 2004/0092879 | A1 | | 5/2004 | Kraus et al. | |
| 2010/0300451 | A1 | | 12/2010 | Griffith et al. | |
| 2011/0028904 | A1 | * | 2/2011 | Watanabe | A61M 16/0486 604/164.01 |
| 2018/0280647 | A1 | | 10/2018 | Schnell | |

* cited by examiner

DEVICE FOR PERCUTANEOUS DILATIONAL TRACHEOTOMY

CROSS-REFERENCE TO RELATED APPLICATIONS

This application is a National Stage of International Application No. PCT/EP2021/053808 filed Feb. 17, 2021, which claims benefit of German Patent Application No. 10 2020 105 048.8 filed Feb. 26, 2020, each of which are herein incorporated by reference in their entirety.

TECHNICAL FIELD

The present invention relates to a device for percutaneous dilational tracheostomy, wherein the device comprises a puncture needle, a guide catheter, and a guidewire. The present invention also includes a set comprising the device according to the invention for percutaneous dilational tracheostomy, as well as a dilator for expanding the tracheostoma and, as further components, optionally a scalpel, a predilator, an insertion aid for the guidewire, a reinforcement catheter with a safety lock for the guidewire, a set of compresses and/or a syringe.

BACKGROUND

Percutaneous dilatative tracheostomy is a method of inserting a tracheostomy tube into a patient's windpipe. As an alternative to the surgical method, the trachea is initially accessed here using an over-the-needle catheter. This typically takes place between the 2nd and the 3rd or the 3rd and the 4th tracheal ring.

The individual components necessary for percutaneous dilatative tracheostomy are typically provided in coordinated sets, which, in addition to the over-the-needle catheter, also include other components that can be used in the procedure, such as a scalpel, a predilator, a dilator, a guidewire, an insertion aid for the guidewire, a reinforcement catheter with a safety lock for the guidewire, a set of compresses and/or a syringe.

Over-the-needle catheters consist of a hollow, sharpened steel puncture needle surrounded by a tight-fitting plastic guide catheter. The needle and the catheter both often each have a connector, such as a female Luer connector, at the proximal end facing away from the patient. The puncture needle provides sufficient strength to the guide catheter so that it can be inserted into the patient.

After the over-the-needle catheter has been inserted, the puncture needle is pulled out of the guide catheter remaining in the patient, so that a guidewire, the so-called Seldinger wire, can then be inserted into the trachea through the guide catheter. The guidewire serves as a guide rail during dilatation with dedicated dilators and during the subsequent insertion of the tracheostomy tube. This minimizes the risk of tracheal wall injuries and ensures that the dilators and the tracheostomy tube are actually inserted into the trachea and do not accidentally end up in the via falsa.

After the puncture needle has been pulled out of the guide catheter, there is a risk that the guide catheter remaining in the patient will kink. This can happen easily, particularly if the user tries to change the position or angle of the catheter relative to the position of the trachea after removing the stabilizing puncture needle. Once the guide catheter is kinked, it is often no longer possible to pass the guidewire through the guide catheter because the kink is a constriction through which the guidewire cannot be pushed.

This situation often cannot be fixed even by reinserting the already removed puncture needle, because this can easily lead to the guide catheter being punctured by the reinserted cannula. In many cases, therefore, the puncture procedure is repeated again with a new over-the-needle catheter, and, if no suitable individual components are available to do this, a new tracheostomy set will frequently be opened, which of course involves additional consumption costs.

SUMMARY

To solve the above-described problem, the present invention proposes a device for percutaneous dilational tracheostomy which comprises a puncture needle, a guide catheter and a guidewire, wherein the puncture needle has a ground tip at its distal end, wherein the maximum outer diameter of the puncture needle is smaller than the minimum inner diameter of the guide catheter, and wherein the puncture needle can be inserted so far into the guide catheter that the ground tip of the puncture needle projects beyond the distal end of the guide catheter, wherein the device according to the invention is in particular characterised in that the maximum diameter of the guidewire is smaller than the minimum inner diameter of the puncture needle, so that the guidewire can be passed through the puncture needle such that its end projects beyond the ground tip of the puncture needle.

The advantage of the present invention is that the cross-sections of the puncture needle, the guide catheter and the guidewire are sized such that the guidewire can be passed through the puncture needle disposed in the guide catheter. It is therefore no longer necessary to pull out the puncture needle after the insertion of the guide catheter into the trachea in order to be able to insert the guidewire. When using the device according to the invention, there is consequently also no risk of the catheter kinking, because the catheter is also stabilised by the puncture needle during the insertion of the guidewire.

This advantage cannot be achieved with conventional tracheostomy devices, because the inner diameter of the guide catheter in said devices is just large enough to pass the guidewire through. On the other hand, in conventional tracheostomy devices, the inner diameter of the guide catheter is as small as possible in order to have the overall smallest possible cross-section for the puncture.

For the aforementioned reasons, the inner diameter of the guide catheter in conventional tracheostomy devices is about 0.1 to 0.4 mm larger than the outer diameter of the guidewire. As a result, the outer diameter of the guidewire is larger than the inner diameter of the puncture needle in conventional tracheostomy devices. Therefore, in conventional tracheostomy devices, it is not possible to push the guidewire through the puncture needle.

In contrast, in the present invention, the guide catheter and the puncture needle are dimensioned such that the guidewire can be passed through the puncture needle. For this purpose, in some embodiments of the invention, the guidewire has a maximum diameter in the range of 1.0 to 1.5 mm, preferably in the range of 1.2 to 1.3 mm. In certain embodiments, the minimum inner diameter of the puncture needle is 0.1 to 0.4 mm larger than the maximum diameter of the guidewire. In specific embodiments, the minimum inner diameter of the puncture needle is 0.2 to 0.4 mm larger than the maximum diameter of the guidewire. In certain embodiments of the invention, the minimum inner diameter of the guide catheter is 0.05 to 0.3 mm larger than the maximum outer diameter of the puncture needle. In specific embodiments, the minimum inner diameter of the guide catheter is 0.05 to 0.15 mm larger than the maximum diameter of the puncture needle.

The puncture needle consists of a hollow needle having a ground tip at its distal end. A connector is preferably disposed at the proximal end of the hollow needle. The guide catheter consists of a guide tube, which is preferably tapered at its distal end. A connector is also optionally disposed at the proximal end of the guide tube. The available connectors are suitable for connection to a conventional medical tube system (e.g., female Luer connector).

In the context of the present invention, the terms “distal” and “proximal” are used from the perspective of a physician using the tracheostomy device; i.e., the proximal end of the puncture needle is the end which remains outside the patient’s body after the puncture, while the distal end is inserted through the skin into the patient’s trachea during the puncture.

The ground tip of the puncture needle preferably projects 1 to 10 mm, particularly preferably 2 to 6 mm, beyond the distal end of the guide catheter. The lengths of the hollow needle and the catheter tube, and, if necessary, the position and configuration of the connectors on the puncture needle and the guide catheter, are selected accordingly for this purpose.

The hollow needle of the puncture needle preferably has a length in the range of 4 cm to 9 cm. The maximum outer diameter of the hollow needle is preferably in the range of 1.3 to 2.1 mm. In certain embodiments, the maximum outer diameter of the hollow needle is in the range of 1.5 to 2.0 mm. The minimum inner diameter of the hollow needle is preferably in the range of 1.1 to 1.9 mm. In certain embodiments, the minimum inner diameter of the hollow needle is in the range of 1.2 to 1.8 mm. The wall thickness of the hollow needle is preferably in the range of 0.1 to 0.2 mm.

The catheter tube of the guide catheter preferably has a length in the range of 3 cm to 8 cm. The maximum outer diameter of the catheter tube is preferably in the range of 1.5 to 2.5 mm. In certain embodiments, the maximum outer diameter of the catheter tube is in the range of 1.6 to 2.3 mm. The minimum inner diameter of the catheter tube is preferably in the range of 1.4 to 2.1 mm. In certain embodiments, the minimum inner diameter of the catheter tube is in the range of 1.6 to 1.9 mm. The wall thickness of the catheter tube of the guide catheter is preferably in the range of 0.1 to 0.2 mm.

In preferred embodiments, the hollow needle of the puncture needle is made of metal, particularly preferably of steel. The guide tube of the guide catheter is preferably made of plastic, preferably FEP (fluorinated ethylene propylene). The available connectors on the puncture needle and/or the guide catheter are likewise preferably made of plastic. In particularly preferred embodiments, the guide tube and a connector disposed upon it are integrally formed from a plastic material.

The plastic of the guide tube can consist of either a transparent or non-transparent plastic material, optionally with one or more white or coloured longitudinal stripes to facilitate endoscopic position control. In certain embodiments, the plastic material of the guide tube contains an X-ray contrast agent (e.g., barium sulphate).

In certain embodiments, in which connectors are disposed at the proximal end of the puncture needle and the guide catheter, the connector on the puncture needle is disposed in the connector on the guide catheter in a first stable insertion position such that the ground tip of the puncture needle projects 1 to 10 mm, particularly preferably 2 to 6 mm, beyond the distal end of the guide catheter. In these embodiments, the puncture needle can preferably be brought into a second stable insertion position, in which the ground tip no longer projects beyond the guide catheter, by turning or pulling on the connector of the puncture needle.

In order to bring the puncture needle into a second stable insertion position in which the ground tip does not project beyond the guide catheter by turning, some embodiments comprise an internal or external thread disposed on the inner wall of the guide catheter connector and a corresponding external or internal thread disposed on the outer wall of the puncture needle connector. Alternatively, an internal thread is disposed on the inner wall of the guide catheter connector or on the outer wall of the puncture needle connector and a projecting web or a projecting lug that can engage with the thread located on the other wall is disposed on the respective other wall (outer wall of the guide catheter connector or the inner wall of the puncture needle connector).

The coordinated geometry of the thread(s) or webs/lugs preferably defines at least two different latching positions, wherein the ground tip of the puncture needle is stably held projecting 1 to 10 mm, particularly preferably 2 to 6 mm, beyond the distal end of the guide catheter in a first latching position, and wherein the ground tip of the puncture needle does not project beyond the guide catheter in a second latching position.

The guidewire is preferably made of metal or plastic. A preferred metal for the guidewire is steel, nitinol, or a combination thereof. The embodiments with metal wire preferably have a plastic coating on the metal wire. In certain embodiments, the material of the plastic coating is Teflon (polytetrafluoroethylene) or FEP (fluorinated ethylene propylene). Certain embodiments are characterised in that the end of the guidewire which projects beyond the end of the puncture needle when passed through the puncture needle is curved in a quarter to three-quarter circle. This type of guidewire is often referred to as a guidewire.

To facilitate insertion of the guidewire, in certain embodiments, the lumen of the hollow needle of the puncture needle widens in a funnel shape in proximal direction at the end of the puncture needle opposite to the ground tip.

In embodiments comprising a connector at the proximal end of the puncture needle, the lumen of the connector preferably tapers in a funnel shape in the direction of the lumen of the puncture needle to facilitate insertion of the guidewire into the hollow needle. The inner wall of the connector at the proximal end of the hollow needle is particularly preferably flush with the hollow needle opening.

In an alternative embodiment, in which the lumen of a connector at the proximal end of the puncture needle is substantially cylindrical, an adapter is preferably disposed in a precisely fitting manner in the lumen of the connector, whereby the adapter itself comprises a lumen that tapers in a funnel shape in the direction of the lumen of the puncture needle to facilitate insertion of the guidewire into the hollow needle. The inner wall of the adapter inserted into the connector at the proximal end of the hollow needle is particularly preferably flush with the hollow needle opening.

The present invention relates to a device for percutaneous dilational tracheostomy, wherein the device comprises a puncture needle, a guide catheter, and a guidewire. In certain embodiments, this device is part of a set for percutaneous dilational tracheostomy which further comprises a dilator for expanding the tracheostoma. Such a dilator comprises a dilatation region having a diameter which increases continuously in longitudinal direction, and, in certain embodiments, a guide channel is provided in longitudinal direction in the dilator, the minimum inner diameter of which is larger than the maximum diameter of the guidewire, so that the guidewire can be passed through the guide channel.

In the dilatation region, the outer diameter of the dilator preferably increases to up to 1.2 to 1.5 cm. In preferred embodiments, the minimum inner diameter of the guide channel of the dilator is in the range of 1.0 to 3.0 mm.

In certain embodiments of the set according to the invention, said set additionally comprises a scalpel, a predilator, an insertion aid for the guidewire, a set of compresses, a reinforcement catheter with a safety lock for the guidewire and/or a syringe, as well as optionally a tracheostomy tube and or insertion aids for inserting a tracheostomy tube.

In the embodiments of the set comprising a predilator for expanding the tracheostoma, said predilator has an outer diameter which is larger than the outer diameter of the guide catheter and smaller than the average outer diameter of the dilator, wherein a guide channel is provided in longitudinal direction in the predilator, the minimum inner diameter of which is larger than the maximum diameter of the guidewire, so that the guidewire can be passed through the guide channel, wherein the minimum inner diameter of the guide channel of the predilator is 0.1 to 1.0 mm larger than the maximum diameter of the guidewire.

In the embodiments of the set comprising a reinforcement catheter, said reinforcement catheter has an outer diameter that is smaller than the minimum inner diameter of the dilator, so that the reinforcement catheter can be passed through the guide channel of the dilator. The minimum inner diameter of the reinforcement catheter is larger than the maximum diameter of the guidewire, so that the guidewire can be passed through the reinforcement catheter, wherein the minimum inner diameter of the reinforcement catheter is 0.1 to 1.0 mm larger than the maximum diameter of the guidewire.

In the embodiments of the guidewire comprising an insertion aid for the guidewire, the insertion aid for the guidewire is preferably disposed at the end of the guidewire which projects beyond the end of the puncture needle when passed through the puncture needle, wherein the insertion aid comprises a guide channel in longitudinal direction and centrally, the minimum inner diameter of which is larger than the maximum diameter of the guidewire, so that the guidewire can be passed through the central guide channel, wherein one end of the guide channel opens into a conically tapering section of the insertion aid. This conically tapering portion of the insertion aid is sized and shaped such that this portion can be inserted into the proximal end of the puncture needle with or without a connector or with or without an adapter to facilitate insertion of the guidewire into the hollow needle.

For the purpose of the original disclosure, it should be noted that all of the features as they become apparent to a person skilled in the art from the present description, the drawings and the claims, even if they have been specifically described only in connection with specific other features, can be combined both individually and in any combination with other features or groups of features disclosed here, insofar as this has not been expressly excluded or technical circumstances make such combinations impossible or pointless. A comprehensive, explicit presentation of all conceivable combinations of features is omitted here solely for the sake of brevity and legibility of the description.

BRIEF DESCRIPTION OF THE FIGURES

Individual examples of the aforementioned specific embodiments of the invention are provided with reference to the appended FIGS. 1 to 5, wherein.

DETAILED DESCRIPTION OF PARTICULAR EMBODIMENTS

The following features or combinations of features are shown in detail in the above-mentioned figures.

Figure 1:
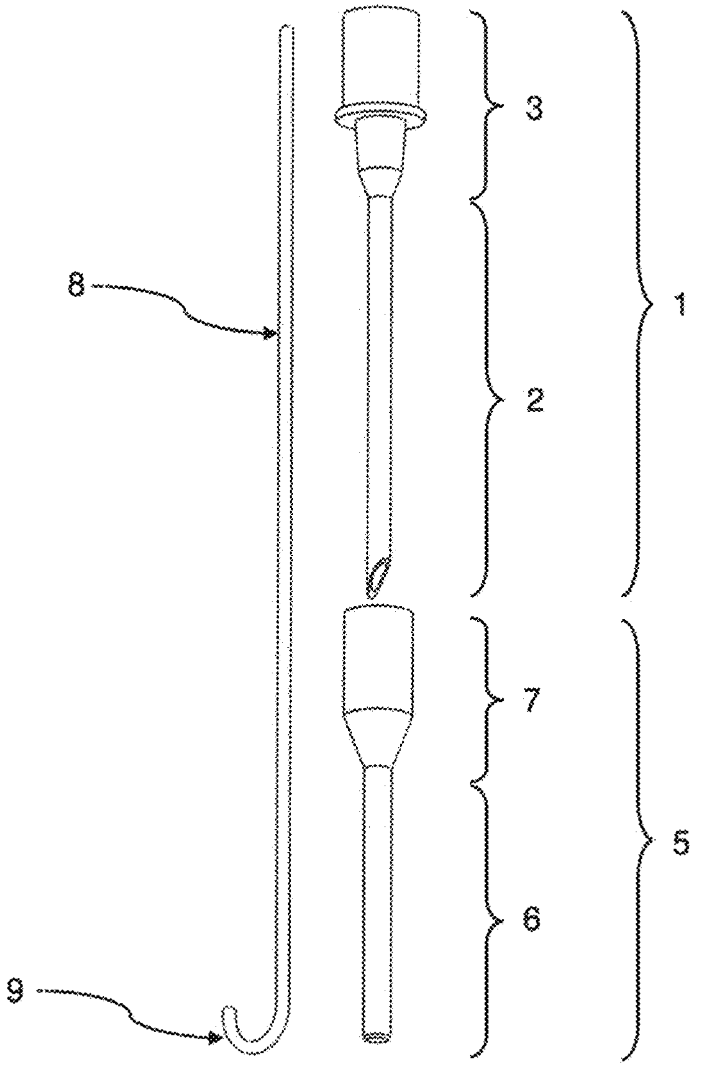
FIG. 1 shows a plan view onto an embodiment of a device according to the invention for percutaneous dilational tracheostomy, wherein the device comprises a puncture needle, a guide catheter and a guidewire having a curved end, and wherein these three components are shown separately, i.e., not inserted into one another.

FIG. 1 shows a plan view onto an embodiment of a device according to the invention for percutaneous dilational tracheostomy, wherein said device comprises a puncture needle 1, a guide catheter 5 and a guidewire 8. In the illustration of FIG. 1, the three components are shown separately, i.e., not inserted into one another. In the illustration of FIG. 1, the puncture needle 1 shows the exposed portion of the hollow needle 2 and also the cannula connector 3 disposed at the proximal end of the puncture needle. As is also common in the conventional puncture needles, a short proximal portion of the hollow needle 2 is surrounded by the cannula connector 3 and the hollow needle 2 is firmly connected to cannula connector 3 via the region which overlaps here.

The guide catheter 5 shown here also consists of two subunits, namely the catheter tube 6 and the catheter connector 7. In the plastic embodiment shown here, the catheter tube and the catheter connector are made in one piece of plastic, so that the plastic material widens conically from the transition from the catheter tube 6 to the catheter connector 7 to then transition in proximal direction into a cylindrical portion.

The guidewire 8 is shown here considerably shortened and comprises a semi-circular curved end at its distal end 9.

Figure 2:
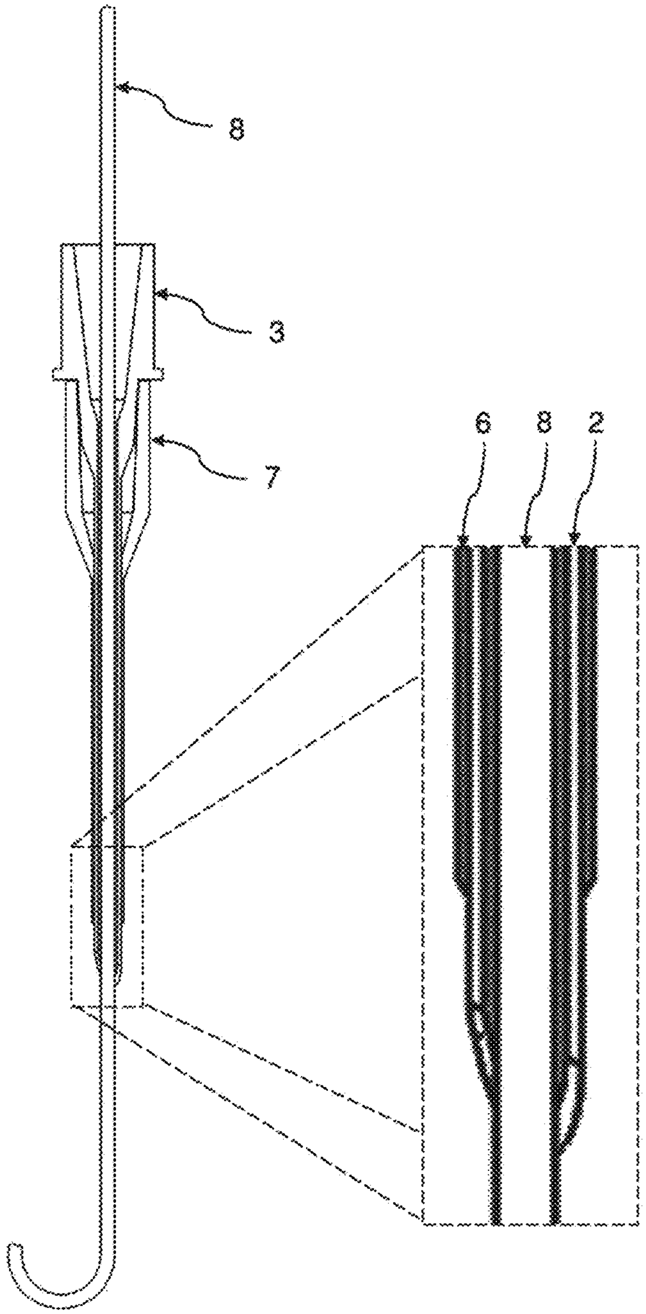
FIG. 2 shows the embodiment of the invention according to FIG. 1 in cross-section, wherein the puncture needle, the guide catheter and the guidewire are shown inserted into one another.

FIG. 2 shows the embodiment of the invention which is broken down into separate components in FIG. 1 in the assembled state in cross-section. It can be clearly seen how the guidewire 8 extends through the hollow needle 2 of the puncture needle and how the hollow needle 2 of the puncture needle is disposed in the catheter tube 6 of the guide catheter. In the assembled state shown here, the distal end of the cannula connector 3 is inserted into the lumen of the catheter connector 7. A stop point provided on the cannula connector defines a position at which the distal end of the hollow needle 2 projects beyond the distal end of the catheter tube 6.

Figure 3:
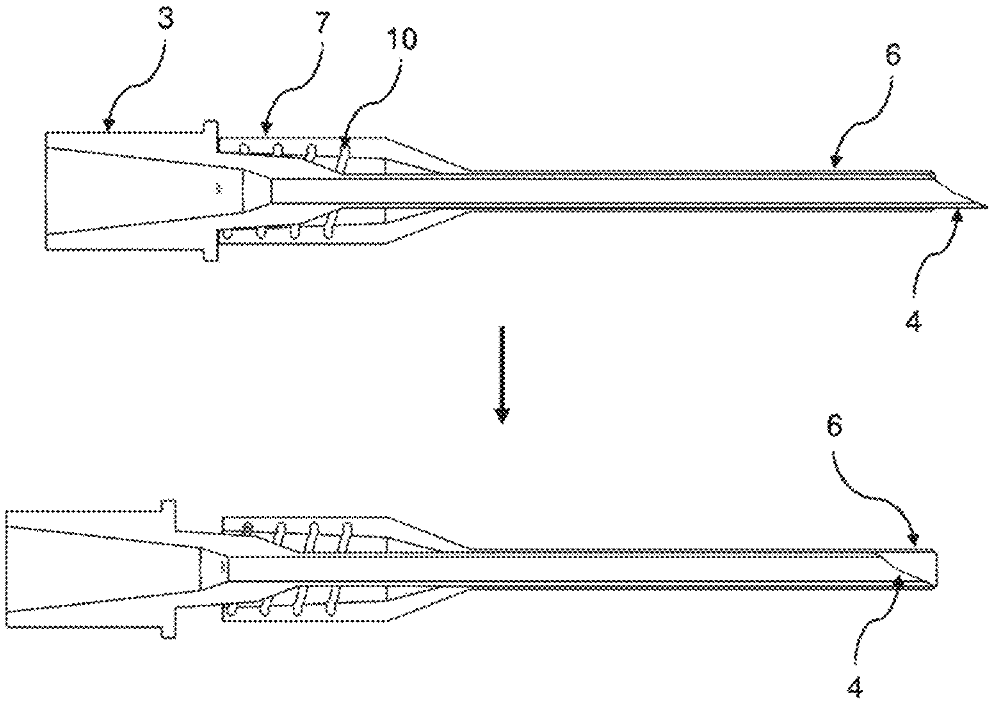
FIG. 3 shows the puncture needle and the guide catheter of an embodiment of the invention in cross-section, wherein the puncture needle is shown inserted into the guide catheter in two different positions.

The cross-sectional view of an embodiment of the invention shown in FIG. 3 shows two discrete stable insertion positions for the puncture needle inserted into the guide catheter. In the state shown above in FIG. 3, the puncture needle is in a first stable insertion position, which, as in the state described above for FIG. 2, is defined by a stop provided on the cannula connector. In this state, the ground tip 4 provided at the distal end of the hollow needle projects beyond the distal end of the catheter tube 6. In the state shown in the lower illustration of FIG. 3, the puncture needle is in a second stable insertion position in which the ground tip 4 at the distal end of the hollow needle does not project beyond the distal end of the catheter tube 6. This second stable insertion position is defined by the internal thread 10 provided on the inner wall of the catheter connector 7. By turning the puncture needle relative to the guide catheter, the puncture needle can thus be moved from the aforementioned first stable insertion position into a second stable insertion position, as a result of which the ground tip 4 at the distal end of the puncture needle is pulled back into the lumen of the guide catheter.

Figure 4:
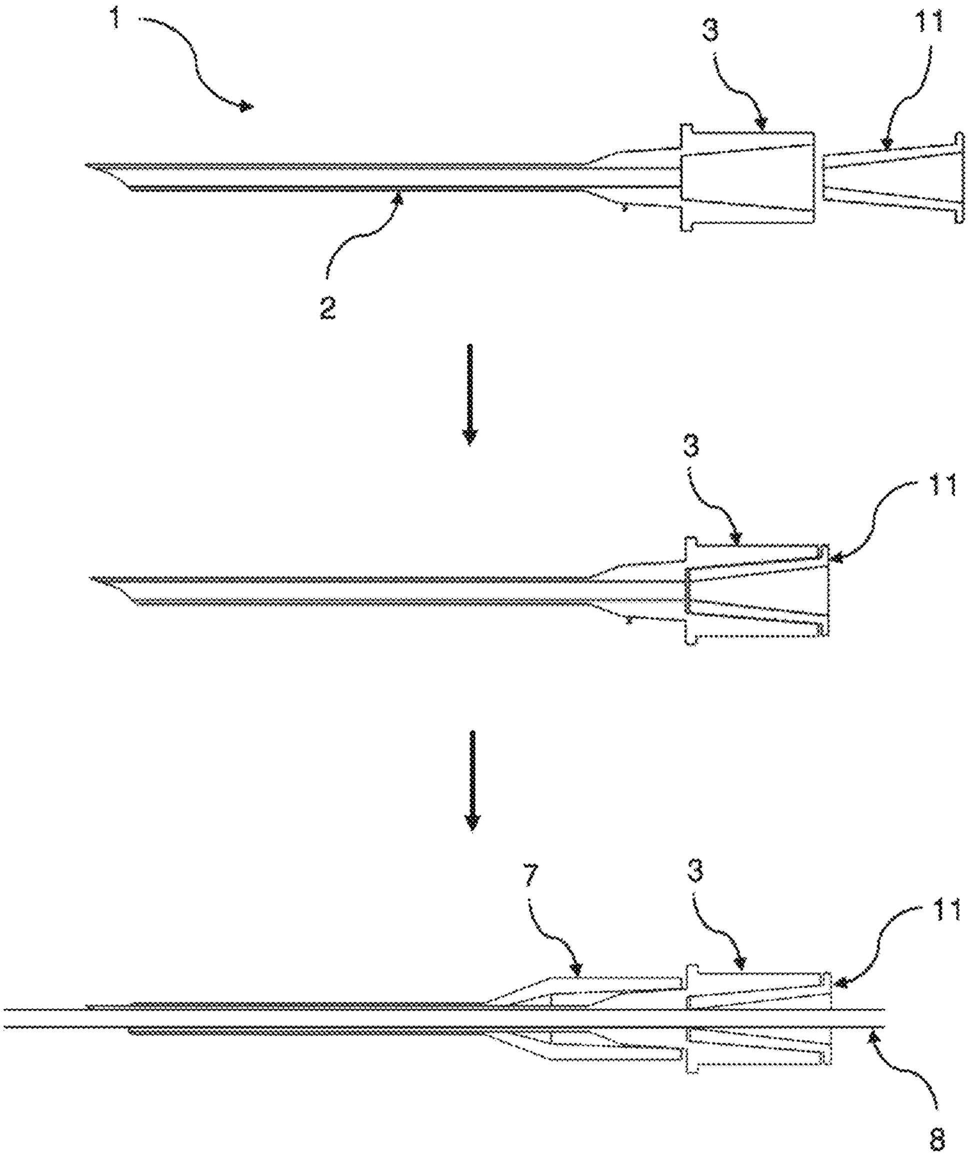
FIG. 4 shows a cross-section through a puncture needle of an embodiment of the invention in three different states, wherein the first two states illustrate how an adapter is inserted into the lumen of the connector disposed at the proximal end of the puncture needle and in the third state the puncture needle is shown with the guidewire passed through the puncture needle and inserted into the guide catheter.

FIG. 4 at the top shows a cross-section through a puncture needle of an embodiment of the invention, in which the inner wall of the cannula connector 3 tapers slightly conically in distal direction to the lumen of the hollow needle 2. However, a portion which extends perpendicular to the longitudinal direction of the hollow needle 2 remains around the proximal end of the hollow needle. When a guidewire is inserted, the end of the guidewire can abut these perpendicular surfaces, which makes it very difficult to insert the guidewire into the hollow needle. To avoid this, in this embodiment, an adapter 11 is provided that can be inserted into the lumen of the cannula connector 3 in a precisely fitting manner (see the figure in the middle), thus eliminating the above-described perpendicular surfaces to the right and the left of the hollow needle entry opening. For this purpose, the adapter 11 comprises a lumen which tapers in a funnel shape in the direction of the lumen of the puncture needle, so that the inner wall of the adapter is flush with the entry opening of the hollow needle 2.

If a guidewire 8 is now inserted into the puncture needle 1, it is guided along the inner wall of the adapter 11 directly into the entry opening of the hollow needle 2, which facilitates the insertion of the guidewire 8 into the puncture needle 1 significantly.

Figure 5:
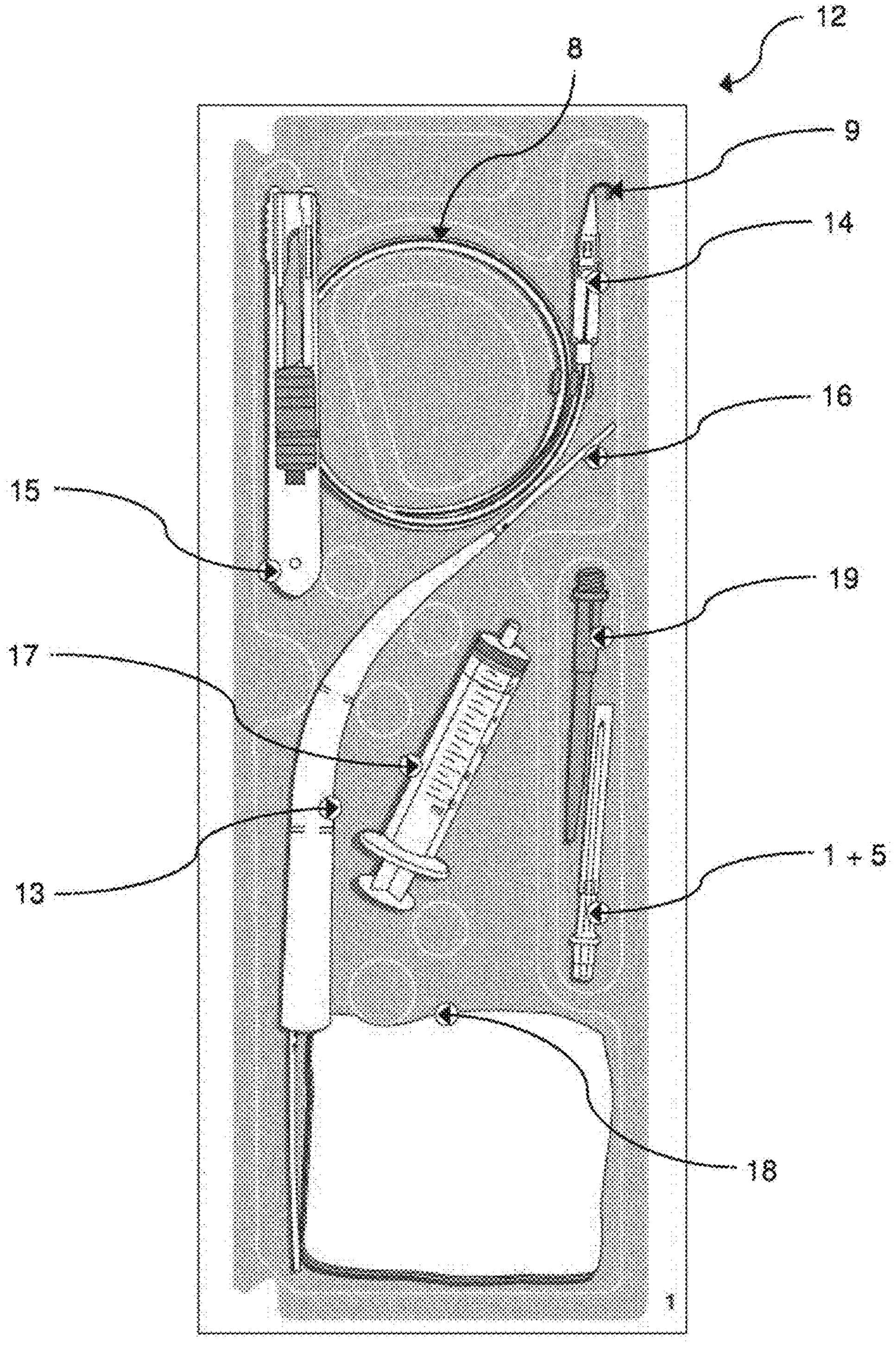
FIG. 5 is a plan view onto an embodiment of a set for percutaneous dilational tracheostomy, wherein the set comprises a puncture needle, a guide catheter and a guidewire, as well as a dilator, a scalpel, a predilator, an insertion aid for the guidewire, a reinforcement catheter with a safety lock for the guidewire, a set of compresses and a syringe.

FIG. 5 shows a plan view onto an embodiment of a set 12 for percutaneous dilational tracheostomy, wherein, in addition to the puncture needle 1, the guide catheter 5 and the guidewire 8, this set 12 further includes a predilator 19, a dilator 13, an insertion aid for the guidewire 14, a scalpel 15, a reinforcement catheter with a safety lock for the guidewire 16, a syringe 17 and a set of compresses 18.

LIST OF REFERENCE SIGNS

1. Puncture needle
2. Hollow needle
3. Cannula connector
4. Ground tip
5. Guide catheter
6. Catheter tube
7. Catheter connector
8. Guidewire
9. Curved end
10. Thread
11. Adapter
12. Tracheostomy set
13. Dilator
14. Insertion aid for the guidewire
15. Scalpel
16. Reinforcement catheter with safety lock
17. Syringe
18. Compresses
19. Predilator

The invention claimed is:

1. A device for percutaneous dilational tracheostomy, comprising:
- a puncture needle including a ground tip at a distal end of the puncture needle, a lumen, and a connector at a proximal end of the puncture needle that defines an entry opening for the lumen, the connector having a perpendicular surface around the proximal end of the puncture needle, the perpendicular surface extending perpendicular to a longitudinal direction of the puncture needle;
- an adapter insertable into the connector at the proximal end of the puncture needle;
- a guide catheter; and
- a guidewire,
- wherein a maximum outer diameter of the puncture needle is smaller than a minimum inner diameter of the guide catheter,
- wherein the puncture needle can be inserted so far into the guide catheter that the ground tip of the puncture needle projects beyond a distal end of the guide catheter,
- wherein a maximum diameter of the guidewire is smaller than a minimum inner diameter of the puncture needle, so that the guidewire can be passed through the puncture needle such that its end projects beyond the ground tip of the puncture needle,
- wherein the connector has a first lumen which narrows in a first funnel shape having a first taper toward the lumen of the puncture needle, and
- wherein the adapter is fittingly insertable into the first lumen of the connector so as to eliminate the perpendicular surface around the entry opening for the lumen of the puncture needle, and the adapter has a second lumen which narrows in a second funnel shape having a second taper toward the lumen of the puncture needle, the second taper being different from the first tape.

2. The device according to claim 1, wherein the guidewire has a maximum diameter in a range of 1.0 to 1.5 mm.

3. The device according to claim 1, wherein the minimum inner diameter of the puncture needle is 0.1 to 0.4 mm larger than the maximum diameter of the guidewire.

4. The device according to claim 1, wherein the minimum inner diameter of the guide catheter is 0.05 to 0.3 mm larger than the maximum outer diameter of the puncture needle.

5. The device according to claim 1, wherein the puncture needle is made of steel.

6. The device according to claim 1, wherein the guide catheter is made of plastic.

7. The device according to claim 1, wherein the guidewire is made of metal or plastic.

8. The device according to claim 1, wherein the guide catheter comprises a catheter connector at a proximal end of the guide catheter, wherein the connector of the puncture needle is configured to be disposed in the catheter connector in a first stable insertion position such that the ground tip of the puncture needle projects 1 to 10 mm beyond the distal end of the guide catheter, and wherein, by turning or pulling on the connector of the puncture needle, the puncture needle is brought into a second stable insertion position in which the ground tip does not project beyond the guide catheter.

9. The device according to claim 1, wherein the end of the guidewire which projects beyond the end of the puncture needle when passed through the puncture needle is curved in a quarter to three-quarter circle.

10. A kit for percutaneous dilational tracheostomy, comprising:

the device according to claim 1; and a dilator for expanding a tracheostoma, wherein the dilator comprises a dilatation region having a diameter which increases continuously in longitudinal direction and wherein a guide channel is provided in longitudinal direction in the dilator, the minimum inner diameter of which is larger than the maximum diameter of the guidewire, so that the guidewire can be passed through the guide channel of the dilator.

11. The kit according to claim 10, further comprising a predilator for expanding the tracheostoma, wherein the predilator has an outer diameter which is larger than the outer diameter of the guide catheter and smaller than an average diameter of the dilator, and wherein a guide channel is provided in longitudinal direction in the predilator, the minimum inner diameter of which is larger than the maximum diameter of the guidewire, so that the guidewire can be passed through the guide channel of the predilator, wherein the minimum inner diameter of the guide channel of the predilator is 0.1 to 1.0 mm larger than the maximum diameter of the guidewire.

12. The kit according to claim 10, wherein, at the end of the guidewire which projects beyond the end of the puncture needle when passed through the puncture needle, an insertion aid is disposed, which comprises a guide channel in longitudinal direction, the minimum inner diameter of which is larger than the maximum diameter of the guidewire, so that the guidewire can be passed through the guide channel of the insertion aid, wherein one end of the guide channel of the insertion aid opens into a conically tapering section of the insertion aid.

13. The kit according to claim 10, further comprising:

a scalpel, a predilator, a set of compresses, a reinforcement catheter, a tracheostomy tube, one or more insertion aids for the tracheostomy tube, and/or a syringe.

* * * * *